(12) United States Patent
Summers, III et al.

(10) Patent No.: US 10,246,380 B2
(45) Date of Patent: Apr. 2, 2019

(54) SOLID WASTE TREATMENT METHOD

(71) Applicant: B.A.M.2 Waste Water Consulting, Ptr., Springfield, TN (US)

(72) Inventors: Buford H. D. Summers, III, Dresden, TN (US); Sidney Lattimore, Jr., Macon, GA (US)

(73) Assignee: B.A.M.2 Waste Water Consulting, Ptr., Springfield, TN (US)

( * ) Notice: Subject to any disclaimer, the term of this patent is extended or adjusted under 35 U.S.C. 154(b) by 0 days.

(21) Appl. No.: 15/450,492

(22) Filed: Mar. 6, 2017

(65) Prior Publication Data

US 2017/0334796 A1 Nov. 23, 2017

Related U.S. Application Data

(63) Continuation-in-part of application No. 15/156,985, filed on May 17, 2016, now Pat. No. 9,630,888.

(51) Int. Cl.

| | |
|---|---|
| *B09B 3/00* | (2006.01) |
| *C05F 3/00* | (2006.01) |
| *C05F 5/00* | (2006.01) |
| *C05F 3/04* | (2006.01) |
| *A61L 2/18* | (2006.01) |
| *C02F 9/00* | (2006.01) |
| *C02F 11/02* | (2006.01) |
| *C02F 1/74* | (2006.01) |
| *C02F 1/76* | (2006.01) |
| *C02F 3/02* | (2006.01) |
| *C02F 3/34* | (2006.01) |
| *C02F 103/00* | (2006.01) |
| *C02F 103/20* | (2006.01) |
| *C02F 1/52* | (2006.01) |
| *C02F 1/66* | (2006.01) |

(52) U.S. Cl.
CPC .................... *C05F 3/00* (2013.01); *A61L 2/18* (2013.01); *C02F 9/00* (2013.01); *C02F 11/02* (2013.01); *C05F 3/04* (2013.01); *C05F 5/00* (2013.01); *C05F 5/008* (2013.01); *C02F 1/52* (2013.01); *C02F 1/66* (2013.01); *C02F 1/74* (2013.01); *C02F 1/76* (2013.01); *C02F 3/02* (2013.01); *C02F 3/34* (2013.01); *C02F 2103/005* (2013.01); *C02F 2103/20* (2013.01); *C02F 2209/29* (2013.01); *C02F 2301/106* (2013.01); *C02F 2303/04* (2013.01); *C02F 2303/185* (2013.01); *Y02A 40/205* (2018.01); *Y02A 40/207* (2018.01); *Y02A 40/212* (2018.01); *Y02P 20/145* (2015.11); *Y02W 10/15* (2015.05); *Y02W 10/37* (2015.05)

(58) Field of Classification Search
CPC ................. B09B 3/00; C05F 3/00; A61L 2/18
USPC .................................................. 588/313, 405
See application file for complete search history.

(56) References Cited

U.S. PATENT DOCUMENTS

| | | | |
|---|---|---|---|
| 3,915,853 A | 10/1975 | Luck | |
| 5,240,600 A | 8/1993 | Wang et al. | |
| 6,146,531 A | 11/2000 | Matheson | |
| 7,481,940 B2 | 1/2009 | Clifford, III et al. | |
| 7,566,400 B2 | 7/2009 | Harmon et al. | |
| 7,727,397 B2 | 6/2010 | Gerardi et al. | |
| 8,192,626 B2 | 6/2012 | Theodore et al. | |
| 8,597,513 B2 | 12/2013 | Borole et al. | |
| 9,630,888 B1 * | 4/2017 | Lattimore, Jr. | ........... C05F 3/00 |
| 9,688,584 B2 | 6/2017 | Bhalla et al. | |
| 9,771,287 B2 | 9/2017 | Anker et al. | |
| 2013/0186155 A1 | 6/2013 | Blaine | |
| 2013/0193068 A1 | 8/2013 | Jones et al. | |
| 2014/0116938 A1 | 5/2014 | Theodore | |

FOREIGN PATENT DOCUMENTS

| | | |
|---|---|---|
| CN | 102557274 A | 7/2012 |
| CN | 203124392 U | 8/2013 |
| WO | WO 1990/15028 A1 | 12/1990 |

OTHER PUBLICATIONS

International Search Report and Written Opinion dated Jul. 31, 2017 for Application No. PCT/US2017/032892, 11 pgs.

* cited by examiner

*Primary Examiner* — Edward M Johnson
(74) *Attorney, Agent, or Firm* — Frost Brown Todd, LLC

(57) ABSTRACT

A solid waste treatment method includes the steps of: degradation and sterilization via chlorination of the solid waste, stabilization of the solid waste and regeneration of biomass to reduce or eliminate solid waste. The solid waste treatment method may be utilized in agricultural, industrial or municipal settings.

15 Claims, 3 Drawing Sheets

SOLID WASTE TREATMENT METHOD

PRIORITY

This application is a continuation-in-part of U.S. patent application Ser. No. 15/156,985, filed May 17, 2016, entitled "Sanitary Waste Treatment Method," the disclosure of which is incorporated by reference herein.

Industrial, municipal and agricultural waste may include solid waste. Industrial sources of solid waste include the beer brewing process, which generates large amounts of wastewater effluent and solid wastes (e.g., spent grains, trub, spent yeast, diatomaceous earth, etc.). Municipal sources of solid waste may include human waste, household waste and run-off from streets. Agricultural sources of solid waste include manure generated on farms, in feedlots, in dairies, etc. Regardless of the source of solid waste, it must be treated and/or disposed in accordance with regulations set by governmental entities.

Although anaerobic microbes are commonly used to oxidize the organic constituents in solid waste, some have attempted to avoid the afore-mentioned problems by treating solid waste aerobically. For example, utilizing an aerobic manure treatment process, aerobic microorganisms that are already present in the manure oxidize bio-available organic and nitrogenous compounds, resulting in reduced odor and ammonia emissions. However, aerobic treatment is not widely utilized for the treatment of manure primarily due to the costs associated with operating the motors, compressors or fans required to supply enough oxygen to support the aerobic bacteria.

Sterilization is often one of the last steps in the tertiary treatment of water containing human waste. The purpose of the sterilization step is to substantially reduce the number of microorganisms in the water, which is to be discharged back into the environment for the later use of bathing, drinking, irrigation, etc.

Chlorination is the most common form of waste water sterilization in North America. However, disadvantages of chlorination at the end of waste water treatment may include chlorination of residual organic material, which can generate chlorinated-organic compounds that may be carcinogenic or harmful to the environment. Moreover, residual chlorine or chloramines may also be capable of chlorinating organic material in the natural aquatic environment. Further, because residual chlorine may be toxic to aquatic species, the treated effluent must also be chemically dechlorinated, adding to the complexity and cost of treatment.

While a variety of solid waste treatment methods have been devised and utilized in industrial, municipal and agricultural settings, it is believed that no one prior to the inventor(s) has devised or used a solid waste treatment method as described herein, which surprisingly comprises seemingly disparate and/or disadvantageous steps to decontaminate the solid waste so that is suitable for re-use or disposal.

BACKGROUND

The disclosed method comprises seemingly disparate and/or disadvantageous steps of at least partially sterilizing the solid waste and then re-introducing aerobic and/or facultative bacteria; these steps are seemingly disparate and/or disadvantageous for at least the following reasons. First, sterilization of solid waste indiscriminately kills microbes (including microbial spores) whether they are harmful or helpful to decontaminating the solid waste (e.g., anaerobic, aerobic and facultative bacteria). Second, by killing microbes, further contaminants are released into the solid waste, including organic compounds and nitrogen. Third, by inoculating sterilized solid waste with aerobic and/or facultative bacteria, one would expect to incur significant costs associated with sufficiently aerating the solid waste so that the added bacteria are effective. Fourth, at least partial sterilization through chlorination may generate undesired byproducts.

Despite the foregoing, the inventors have surprisingly found that by combining the steps of at least partial degradation and sterilization through chlorination and inoculation with aerobic and/or facultative bacteria, that a simple, effective and inexpensive method of decontaminating solid waste is achieved. The disclosed method may advantageously eliminate the need to undertake primary sedimentation and/or secondary treatment, which may in turn require cost intensive construction and use of physical structures, for example, filters, screens biotowers, rotating contactors, media beds and the like. Moreover, the method may be utilized in industrial and agricultural settings as well as in municipal solid waste treatment systems.

BRIEF DESCRIPTION

In some embodiments, a method of treating solid waste comprises the steps of: chlorinating solid waste having a first biological oxygen demand to produce degraded and sterilized solid waste and residual solid waste; measuring the residual solid waste for chlorine residuals, and if residual chlorine is: present, dechlorinating the residual solid waste to produce dechlorinated residual solid waste; or not present, determining that the residual solid waste is dechlorinated residual solid waste; adding a flocculating composition to the dechlorinated residual solid waste to solubilize the dechlorinated residual solid waste; and inoculating the dechlorinated residual solid waste with bacteria, selected from the group of aerobic bacteria, facultative bacteria and combinations thereof, wherein the bacteria biodegrade the dechlorinated residual solid waste.

In some embodiments, a method of treating solid waste comprises the steps of: at least partially degrading and at least partially sterilizing the solid waste by adding chlorine to the solid waste to create residual solid waste; neutralizing the residual solid waste by adding a flocculating composition to the residual solid waste; inoculating the neutralized residual solid waste with bacteria selected from the group of aerobic bacteria, facultative bacteria and combinations thereof; and biodegrading the neutralized residual waste with the bacteria.

In some embodiments, a method treatment of solid waste having a first BOD value, wherein the method consists essentially of: partially degrading and at least partially sterilizing the solid waste by adding chlorine to the solid waste to create residual solid waste; adding a flocculating composition to the residual solid waste; neutralizing the pH of the residual solid waste; inoculating the residual solid waste with bacteria selected from the group of aerobic bacteria, facultative bacteria and combinations thereof; and biodegrading the neutralized residual waste with the bacteria to produce water having a second BOD that is at least 50% less than the first BOD.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawing and photos, in which like reference numerals identify the same elements and in which:

Figure 1:
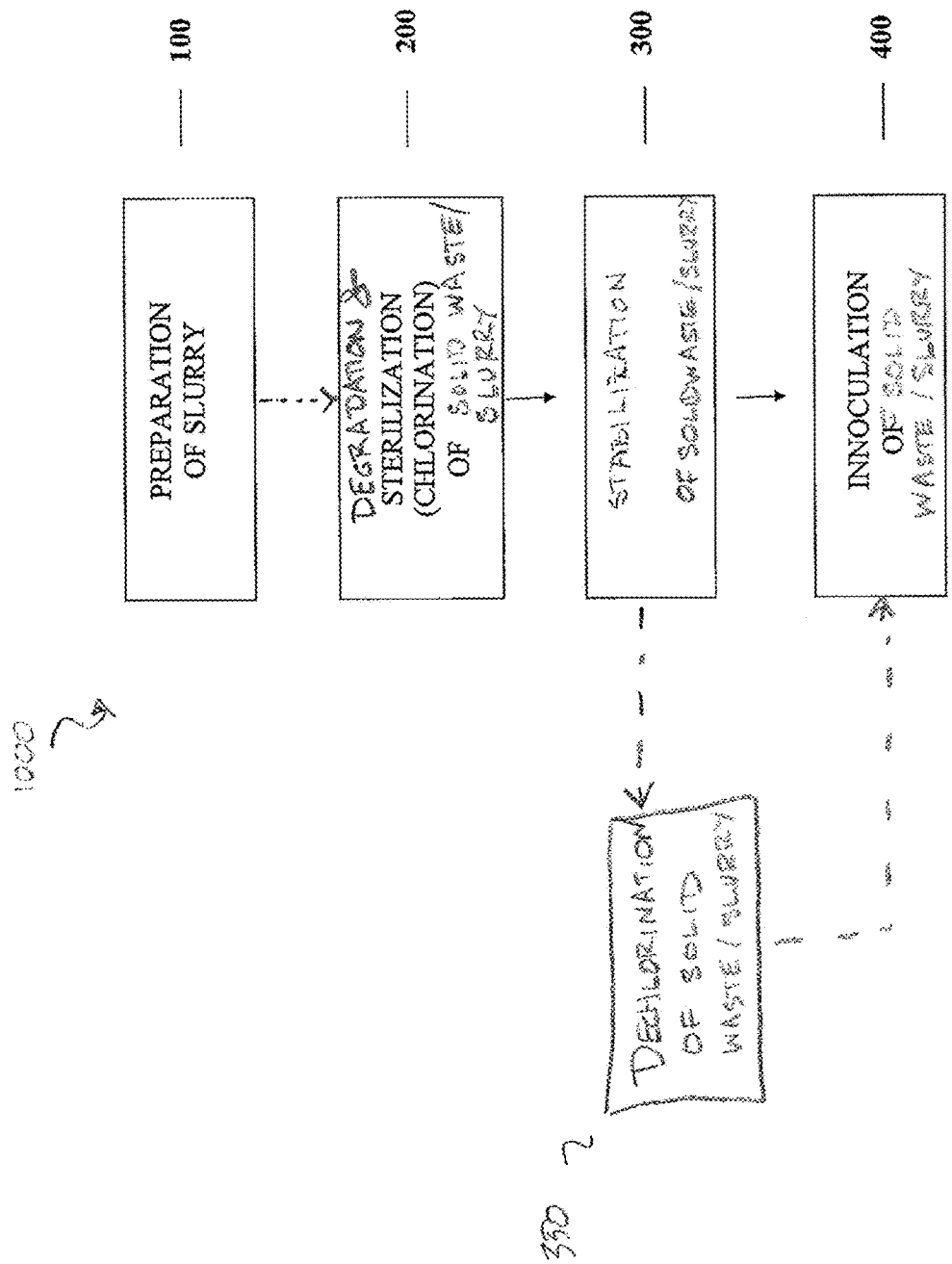
FIG. 1 is a schematic diagram showing the steps in a method of treating solid waste according to the disclosure.

The drawings and photos are not intended to be limiting in any way, and it is contemplated that various embodiments of the method may be carried out in a variety of other ways, including those not necessarily depicted in the drawing. The accompanying drawing is incorporated in and forms a part of the specification, and illustrates several aspects of the present method, and together with the description serve to explain the principles of the method; it being understood, however, that this method is not limited to the precise arrangements shown.

DETAILED DESCRIPTION

All percentages, ratios and proportions used herein are by weight percent of the composition, unless otherwise specified. All average values are calculated "by weight" of the composition or components thereof, unless otherwise expressly indicated.

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawing and descriptions should be regarded as illustrative in nature and not restrictive.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." All numerical ranges disclosed herein are inclusive and combinable.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Having shown and described various embodiments of the present method, further adaptations of the methods and systems described herein may be accomplished by appropriate modifications by one of ordinary skill in the art without departing from the scope of the present method. Several of such potential modifications have been mentioned, and others will be apparent to those skilled in the art.

For instance, the examples, embodiments, geometrics, materials, dimensions, ratios, steps, and the like discussed above are illustrative and are not required. Accordingly, the scope of the present method should be considered in terms of the following claims and is understood not to be limited to the details of structure and operation shown and described in the specification and drawings.

"Biodegraded" as used herein means solid waste and/or or components of solid waste, that have been at least partially or totally broken down to a molecular level through consumption by microorganisms, e.g., bacteria. "Biodegradation" as used herein refers to the process of at least partially or totally breaking solid waste and/or components of solid waste down to a molecular level.

"Biological receptacle" as used herein means any receptacle that will sufficiently contain solid waste before, after or during, treatment of the solid waste with biological agents, e.g., microbes, enzymes, etc. Non-limiting examples of biological receptacles include: chambers, lagoons, tanks, retention ponds and the like.

"Chlorination receptacle" as used herein means any receptacle that will sufficiently contain solid waste before, after or during, chlorination of the solid waste. Non-limiting examples of chlorination receptacles include: chambers, lagoons, tanks, retention ponds and the like.

"Dechlorination receptacle" as used herein means any receptacle that will sufficiently contain solid waste before, after or during, dechlorination of the solid waste. Non-limiting examples of dechlorination receptacles include: chambers, lagoons, tanks, retention ponds and the like.

"Degraded" as used herein means solid waste that has been at least partially or totally been disintegrated into smaller components. "Degradation" as used herein refers to the process of at least partially breaking solid waste down into smaller components.

"Holding receptacle" as used herein means any receptacle that will sufficiently contain solid waste before, after or during, a solid waste treatment step. Non-limiting examples of holding receptacles include: chambers, lagoons, tanks, retention ponds and the like.

"Slurry" as used herein means a suspension of solid waste in a liquid, e.g., water.

"Solid waste" and "sludge" are used interchangeably herein to mean municipal solid waste, including waste excreted by an animal or human, solid waste from industrial processes, solid waste from agricultural processes and combinations thereof. "Solid waste" includes both solid matter and some liquid, e.g., water.

"Sterilization" as used herein means a process that destroys and/or inactivates microbes by chemical and/or physical means. "Sterilization" as used herein encompasses partial sterilization or total sterilization.

"Sterilized" as used herein describes destroyed and/or inactivated microbes. "Sterilized" as used herein encompasses the terms "partially sterilized" or "totally sterilized."

The methods described herein may comprise, consist of or consist essentially of the following steps, elements, formulations and other features as set forth in the present disclosure, as well as any additional or optional steps, elements, formulations and other features described herein or that are otherwise useful in relation to the aforementioned methods.

Referencing FIG. 1, in some embodiments, the method (1000) may comprise one or more of the following steps:

I. Preparation of a Slurry

Referencing FIG. 1, Step 1 (100), in some embodiments if the solid waste does not have a sufficient liquid content to enable efficient treatment of the solid waste, it may be advantageous to make a slurry by mixing liquid, e.g., water, into the solid waste to be treated. In some embodiments, the slurry may comprise from about 50% to about 95%, from about 60% to about 95% or from about 75% to about 95% liquid. In some embodiments, the slurry may comprise about 50% liquid, about 60% liquid, about 75% liquid, or about 95% liquid. In some embodiments, the slurry may be stored or made when it is present in a holding receptacle.

In some embodiments, it may be desirable for the slurry to have a pH of from about 6.5 to about 8.0. In these embodiments, if the pH of the slurry is not already at a pH of from about 6.5 and about 8.0, it may be adjusted using methods known to those of skill in the art. In some embodiments, the slurry may have, or be adjusted to have, a pH of about 6.5, a pH of about 7.0 or a pH of about 8.0.

In embodiments in which the waste contains enough liquid, it need not be made into a slurry prior to being treated. For this reason, in the following method steps described herein below, "solid waste," "sludge" and "slurry" are used interchangeably.

II. Degradation and Sterilization Via Chlorination of Solid Waste

Referencing FIG. 1, Step 2 (200), solid waste is degraded. Degradation of the solid waste may be achieved through intensive chlorination. Chlorination degrades the solid waste and at least partially kills and/or inactivates any microbes in the solid waste. Such microbes may include, but are not limited to: bacteria, viruses, parasites, fungi, protista, archae, plants (e.g., algae) and combinations thereof. Without wishing to be bound by theory, it is believed that chlorination of the solid waste kills microbes present in the solid waste, which may in turn result in their breakdown and release of their organic constituents. The organic constituents may then serve as food for living microorganisms that remain viable in the solid waste, and/or are later added to the solid waste.

In some embodiments, chlorination of the solid waste may be quantified by one skilled in the art by measuring the percentage of microbes killed in a given sample. In some embodiments, the sterilization may be quantified via a direct microscopic count (DMC) method.

In some embodiments, the solid waste is sterilized via chlorination, meaning that from about 50% to about 100% of the microbes are destroyed or inactivated. In some embodiments, the solid waste may be sterilized by at least about 50%, at least about 60%, at least about 70%, at least about 80%, at least about 90%, at least about 95%, at least about 98%, at least about 99% sterilized, or about 100% sterilized. In some embodiments, it is preferred to sterilize the solid waste by at least about 95%.

The solid waste to be chlorinated may remain in the holding receptacle or may be transferred to a chlorination receptacle, such as via gravity feed and/or pumped.

The solid waste may be chlorinated by adding a chlorine-containing compound to the solid waste until the chlorine breakpoint is met. Chlorine containing compounds may be added to the solid waste in gas, liquid and/or solid form. Useful chlorine containing compounds may be selected from the group consisting of the following commercially available compounds: calcium hypochlorite, sodium hypochlorite and combinations thereof.

To degrade the solid waste via chlorination, the solid waste may be treated with one or more doses of the chlorine containing compound. For example, as described below, chlorinating the solid waste may begin with the addition of a first dose of a chlorine containing compound to the solid waste, and after a given time period, observing the sample to determine if the solid waste has been broken down into smaller component parts.

To estimate how much chlorine to add to the solid waste, one of skill in the art may measure or estimate its biochemical oxygen demand ("BOD") and/or chemical oxygen demand ("COD"). BOD and COD may be measured by one skilled in the art utilizing EPA standard methods. For example, BOD may be measured using EPA Standard Method 5210 B, i.e., the "5-Day BOD Test," which is incorporated herein by reference. BOD values may be expressed in milligrams of oxygen consumed per liter of sample ("mg/L") during 5 days of incubation at 20° C.

The first or "initial" BOD of solid waste may vary depending upon the source of the solid waste. For example, a slurry comprising human sanitary waste may have a first BOD of at least about 100 mg/L, at least about 200 mg/L, at least about 300 mg/L, at least about 400 mg/L, at least about 500 mg/L, at least about 1,000 mg/L, at least about 5,000 mg/L or at least about 10,000 mg/L. In a further example, a slurry comprising livestock sanitary waste may have a first BOD value that is substantially higher, e.g., at least about 2,000 mg/L, at least about 3,500 mg/L, at least about 5,000 mg/L or at least about 10,000 mg/L. In a further example, a slurry comprising solid waste from a brewery may have a first BOD value that is at least about 2,400 mg/L, at least about 5,000 mg/L, at least about 9,000 mg/L or at least about 11,000 mg/L.

Depending upon the anticipated or measured BOD of the solid waste to be treated, a first dose of chlorine is added to the solid waste. The first dose may be from about 100 ppm to 3,000 ppm, from about 300 to about 2,000 ppm, or from about 500 to about 1,500 ppm of a chlorine containing compound. In some embodiments, the first dose may be sufficient to completely degrade the solid waste. However, additional doses may be added as needed to degrade the solid waste.

In some embodiments, the chlorinated solid waste may be agitated in order to increase exposure of the solid waste to the chlorine. Agitation may be accomplished using means known to those of skill in the art, including, but not limited to via an impeller aerator, a venturi pump, a vertical aerator and combinations thereof.

In circumstances in which the solid waste to be chlorinated has already been treated with a chlorine-containing substance in order to reduce odor, a smaller first dose of a chlorine-containing compound may suffice. In any case, once the solid waste has been chlorinated, in some embodiments, it may be desirable to re-adjust the pH of the solid waste so that it is from about 6.5 to about 8.0, using methods known to those of skill in the art. In some embodiments, the pH of the solid waste may be re-adjusted to be about 6.5, about 7.0 or about 8.0.

During or after the first dose of chlorine-containing compound is added to the solid waste, the solid waste may be agitated for a suitable length of time, e.g., up to about 24 hours. Without wishing to be bound by theory, it is believed that agitation via aeration of the solid waste after a dose of chlorine is added thereto, may additionally allow for stabilization of the resulting biological trauma to the microbes contained in the solid waste. In some embodiments, aerating the solid waste may be accomplished using: an impeller aerator, a venturi pump, a vertical aerator and combinations thereof.

III. Stabilization of Solid Waste

Referencing FIG. 1, Step 3 (300), after the solid waste is degraded, any residual solid waste is then stabilized to produce a neutral, naturalized condition in which a healthy biomass may be established to digest any residual solids remaining after the degradation step.

If no chlorine residuals remain in the residual solid waste after the residual solid waste is sufficiently degraded through chlorination, then dechlorination of the residual solid waste may not be necessary in order to produce a neutral, naturalized condition into which bacteria are added. However, if sufficient chlorine residuals remain, then the residual solid waste may be dechlorinated pursuant to step (350).

Without wishing to be bound by theory, it is believed that dechlorination of chlorinated residual solid waste may eliminate an environment in the solid waste that is not conducive to microbe stability and/or multiplication. In some embodiments, the pH of the residual solid waste is maintained in a neutral during the dechlorination, whereas in other embodiments, it may be adjusted after dechlorination. In any case, the pH of the residual solid waste may be maintained, or adjusted to, a range of from about 6.5 to about 8.0, using methods known to those of skill in the art. In some embodiments, the pH of the residual solid waste may be maintained at, or adjusted to, about 6.5, about 7.0 or about 8.0 using methods known to those of skill in the art.

A sample of the residual solid waste may be collected in order to measure for total chlorine residuals. The amount of total chlorine residuals may be expressed in ppm of chlorine. The total chlorine residuals may be measured using any method or means known to one of skill in the art. For example, total chlorine residuals may be measured using a color-wheel test kit, or a digital colorimeter. A digital colorimeter that is useful for measuring total chlorine residuals is the Hach Pocket Colorimeter II (Chlorine Free and Total) from the Hach Company (Loveland, Colo.); this colorimeter may be used to measure total chlorine residuals as follows. DPD tablets, powder or liquid (available from USA BlueBook (Waukegan, Ill.)) are added into a vial of sample water taken from the solid waste. The sample is shaken to mix the DPD with the water, which will turn the water pink. The vial is inserted into the colorimeter, which reads the intensity of the color change by emitting a wavelength of light and automatically determining and displaying the color intensity digitally, which reflects the total chlorine residuals. The color measurement range of the colorimeter is from 0 to 4 mg/L, which is equivalent to 0 to 4 ppm of total chlorine residuals.

Prior to dechlorination of the residual solid waste, it may be transferred for example via gravity feed and/or pumped, to a dechlorination receptacle. In any case, the residual solid waste is dechlorinated using any suitable step that will at least partially, or totally, dissipate the total chlorine residuals from the chlorinated solid waste. Suitable methods may be selected from the group of: adding a sulfur containing compound to the chlorinated solid waste, exposing the chlorinated solid waste to ultraviolet light (e.g., sunlight), aeration and combinations thereof.

In embodiments in which the residual solid waste is dechlorinated by adding a sulfur containing compound, the sulfur containing compound may be selected from the following group of commercially available compounds: sodium bisulfate, potassium bisulfate, sulfur dioxide and combinations thereof. As a general rule of thumb, the chlorinated residual solid waste may be dechlorinated by adding a sulfur containing compound in a molar ratio of about 1:1 with the chlorine containing compound that was previously added in the chlorination step to chlorinate the solid waste.

Like in the chlorination of the solid waste, dechlorination of any residual solid waste may be achieved by adding one or more doses of a sulfur containing compound to the chlorinated solid waste. For example, as described below, dechlorinating the chlorinated solid waste may begin with the addition of a first dose of a sulphur containing compound to the chlorinated solid waste, and after a given time period, measuring a sample of the solid waste for total chlorine residuals.

Once a first dose of sulfur containing compound is added to the residual solid waste, it may be aerated a suitable length of time, e.g., up to about 24 hours. Without wishing to be bound by theory, it is believed that aeration of the residual solid waste after a dose of sulfur containing compound is added thereto, drives dissipation of chlorine from the solid waste. In some embodiments, aerating the residual solid waste may be accomplished using: an impeller aerator, a venturi pump, a vertical aerator, forced air, diffused air, injected air and combinations thereof. A sample of the dechlorinated residual solid waste is then collected in order to measure for total chlorine residuals.

If greater than 1.0 ppm, greater than 1.2 ppm or greater than 1.5 ppm of total chlorine residuals are present in the sample of water taken from the chlorinated solid waste, then a second dose of a sulfur containing compound may be added to the solid waste. The solid waste may then be aerated for a suitable length of time, e.g., up to about another 24 hours, at which point the total chlorine residuals are again measured. This process may be repeated as needed until the total chlorine residuals are present in a concentration of less than about 1.0 ppm, less than about 0.8 ppm or less than about 0.5 ppm.

If no chlorine residuals remain in the residual solid waste after the solid waste is sufficiently degraded through chlorination, then dechlorination of the solid waste may not be necessary in order to produce a neutral, naturalized condition into which bacteria are added, in which case step 350 is not necessary prior to inoculation of the solid waste.

In any case, once the residual solid waste contains little or no chlorine residuals, the residual solid waste is stabilized through the additional of a composition that contains precipitation agents, such as iron salts or aluminum salts, which react with, flocculate and/or precipitate impurities in the solid waste, such as phosphates. Exemplary "flocculating compositions" include the compositions described in U.S. Pat. No. 7,384,573B2, entitled, "Compositions for Wastewater Treatment," which is incorporated by reference in its entirety herein.

In some embodiments, the flocculating composition comprises a mixture of about 50-90% calcium carbonate ($CaCO_3$) and 10-50% magnesium carbonate ($MgCO_3$). Preferably, the composition comprises about 75% $CaCO_3$ and about 25% $MgCO_3$. In some embodiments, the flocculating composition of further comprises water, chitosan and acetic acid. For example, a composition comprising about 1-2 parts by weight chitosan, 1-2 parts by weight of a mixture of fine powders of $CaCO_3$ and $MgCO_3$ in a 3:1 ratio, 1-2 parts by weight of glacial acetic acid, and 100 parts by weight of water may be utilized.

In some embodiments, the flocculating composition comprises water, chitosan and acetic acid. An exemplary composition of may comprise about 1-2 parts by weight chitosan, 1-2 parts by weight of a mixture of fine powders of $CaCO_3$ and $MgCO_3$ in a 3:1 ratio, 1-2 parts by weight of glacial acetic acid, and 100 parts by weight of water.

In some embodiments, the flocculating composition comprises comprising a lanthanum salt and a mixture of fine powders of $CaCO_3$ and $MgCO_3$, which preferably is in a 3:1 ratio. Preferably, the lanthanum salt is lanthanum chloride. In a specific embodiment, the composition comprises about 36% to about 60% by weight of lanthanum chloride, and about 7% by weight of a composition comprising a mixture of fine powders of $CaCO_3$ and $MgCO_3$ at a ratio of about 3:1.

Examples of useful commercial flocculating compositions that also neutralize the chlorine include Bio-Clean All Natural Flocculant and/or No-Phos Rare Earth Solution from Bio-Chem Industries, Inc. (Ooltewah, Tenn.). These commercial flocculating compositions may also adjust the pH of the solid waste to a neutral range of from a pH of about 6.8 to a pH of about 7.2.

In a typical solid waste treatment operation, about 2-30 ppm (parts per million of wastewater to be treated) of one of the aforementioned compositions of the are applied to the residual solid waste to achieve acceptable treatment conditions, which include a neutralized pH. Without wishing to be bound by theory, it is believed that the flocculant, is catalyzed by rare earth and/or chitosan blends, which causes flocculation in the water, drawing insoluble material out of insolubility to soluble state, and in turn, buffers the solution toward a neutral pH, that provides favorable conditions for addition of biomass back into the solid waste.

IV. Regeneration of Biomass (Inoculation of Solid Waste)

Referencing FIG. 1, Step 4 (400), stabilized residual solid waste that may contain total chlorine residuals of less about 1 ppm, is inoculated with bacteria selected from the group of aerobic bacteria, facultative bacteria and combinations thereof. Without wishing to be bound by theory, it is believed that the bacteria biodegrade any remaining residual solid waste (i.e., "residual waste"), breaking it down to the molecular level, in some embodiments resulting in clear water. For example, the bacteria may digest the solid waste such that remaining water contains a reduced solids content by weight of the original solids content, wherein the reduction is at least about 25%, at least about 50%, at least about 75%. In some embodiments, the reduction is from about 25% to about 100%, from about 30% to about 90%, from about 50% to about 75%. In some embodiments, the reduction in solid waste is from about 95% to about 100%.

It is further believed that the bacteria utilize any remaining solids as sources of energy, metabolizing components of the degraded solids and converting them into gasses, which may be released into the atmosphere. This is particularly advantageous when treating solid waste that contains manure.

For example, untreated manure releases methane. It is believed that in the regeneration step, the added bacteria digest methane, releasing a hydrogen atom to bind with oxygen to produce water and to produce hydrogen gas that rises to the surface of the water and dissipates.

Untreated manure also releases hydrogen sulfide, which is a colorless gas with the characteristic foul odor of rotten eggs. Hydrogen sulfide is poisonous, corrosive and flammable, and has been responsible for the deaths of numerous dairy farmers and cattle around manure pits. It is believed that in the regeneration step, the bacteria break the hydrogen bond from sulfur, resulting in elemental sulfur, allowing the hydrogen to bond with oxygen, producing water, as well as "off-gassing" the hydrogen in the form of gas bubbles that rise to the surface of the water.

Thus, the present method may produce water and off-gas harmful constituents of the solid matter. Advantageously, this may eliminate the need to remove solid waste to another location for disposal and/or the need to incinerate the solid waste on site. Moreover, the present method may eliminate the need to have multiple biological receptacles (e.g., multiple lagoons on a farm) since the solid waste may be eliminated and more solid waste to be treated subsequently added thereto.

In some embodiments, the stabilized solid waste is moved from the chlorination receptacle to a biological receptacle prior to inoculating the solid waste with the bacteria. In some embodiments, the solid waste may be moved from the chlorination receptacle to the biological receptacle via gravity feed and/or pump. In some embodiments, the stabilized solid waste need not be moved and may be inoculated in the same biological receptacle in which it was chlorinated.

Any suitable source of bacteria may be utilized to inoculate the solid waste. In some embodiments, the bacteria may be sourced from commercially available bioaugmentation products. Examples of useful commercial products include Revive NG (which may optionally be used with Revive S) from Bio-Chem. Industries, Inc. (Ooltewah, Tenn.) and Formula D-500 and Bacteria Supplement D500A for Municipal WWTP, each from USA BlueBook (Waukegan, Ill.).

Like in the stabilization of the solid waste, inoculation of the solid waste may be achieved by adding one or more doses of bacteria to the dechlorinated solid waste. For example, inoculating the solid waste may begin with the addition of a first dose of bacteria. If commercially available bioaugmentation products are utilized, the first dose may be determined based upon the supplier's instructions. In any case, it may not be necessary to limit the amount of bacteria utilized to inoculate the solid waste. As little as about 1 ppm of the bacteria may be added to the solid waste. Any additional bacteria added beyond 1 ppm may enhance the feed-rate of the bacteria, driving the efficiency of the digestion of any residual solid waste.

Example I

Approximately 15 tons of manure are placed in a lagoon having a total surface area of about 80 feet, and an average depth of about 6 feet. The liquid content of the manure is measured and is found to be 75%. Water is added to the manure in a 3:1 ratio and is mixed to form a slurry using a Kasco® Decorative Display Aerator (¾ hp, 1 ph, 240V) from USA BlueBook (Waukegan, Ill.) at full power.

A sample of the slurry is taken from the lagoon. The BOD value of the slurry is measured using EPA Standard Method 5210 B to be 5,100 mg/L.

10 gallons of 60% sodium hypochloride, available as HTH® liquid chlorinator from Lonza Group Ltd. (Muenchensteinerstrasse 38, Switzerland), is added to the slurry. The slurry is continuously mixed as described above for one hour.

The total chlorine residuals of the slurry are measured as follows. A 5 mL aliquot of the slurry and 5 mL of liquid DPD from USA BlueBook (Waukegan, Ill.) are added into a sample cell for a Hach Pocket Colorimeter II (Chlorine Free and Total); the sample cell and pocket colorimeter are each available from the Hach Company (Loveland, Colo.). The sample cell is shaken by hand for 3 minutes. The sample cell is inserted into the pocket colorimeter, which indicates that the total chlorine residuals in the slurry are present at 1.2 ppm.

Another 10 gallons of the 60% sodium hypochloride, available as HTH® liquid chlorinator from Lonza Group Ltd. (Muenchensteinerstrasse 38, Switzerland), is added to the slurry. The slurry is continuously mixed as described above for another hour. The total chlorine residuals of the slurry are measured, as described above, to be present at 1.8 ppm.

The now chlorinated slurry is transferred via gravity feed to a chlorination lagoon having a total surface area of about 80 feet and an average depth of about 6 feet.

The chlorinated slurry is dechlorinated, the remaining solids flocculated and the pH adjusted to a neutral range by adding 1 ppm of Bio-Clean All Natural Flocculant, by weight, for every 1,000 mixed liquor suspended solids ("MLSS") of the waste material being treated, and mixing the slurry as described above for at least 30 seconds.

The slurry is tested for dechlorination as follows. A 5 mL aliquot of the slurry and 5 mL of liquid DPD from USA BlueBook (Waukegan, Ill.) are added into a sample cell for a Hach Pocket Colorimeter II (Chlorine Free and Total); the sample cell and pocket colorimeter are each available from the Hach Company (Loveland, Colo.). The sample cell is shaken by hand for 3 minutes. The sample cell is inserted into the pocket colorimeter, which indicates that the total chlorine residuals in the slurry are present at 0 ppm.

The dechlorinated slurry is transferred via gravity feed to a biological lagoon having a total surface area of about 80 feet and an average depth of about 6 feet.

The slurry is inoculated by adding one gallon each of Revive NG and Revive S from Bio-Chem Industries, Inc. (Ooltewah, Tenn.) per million gallons of slurry. The slurry is mixed 24 hours as described above.

A sample of the inoculated slurry is measured for its BOD value using the 5 Day BOD method. The BOD of the slurry is found to be about 2,200 mg/L.

The slurry is re-inoculated by adding 25 pounds of each of Revive NG and Revive S from Bio-Chem Industries, Inc. (Ooltewah, Tenn.). The slurry is mixed 24 hours as described above.

A sample of the inoculated slurry is measured for its BOD value using EPA Standard Method 5210 B method. The BOD of the slurry is found to be 45 mg/L.

Since the BOD of the inoculated slurry is below 100 mg/L, it may safely be applied to farmland without the risk of contaminating the ground water. Before applying the inoculated slurry to the farmland it is separated into undissolved solids and effluent by clarification settling. The undissolved solids are applied to the farmland and the effluent is subsequently utilized for irrigation or other uses.

Example II

Figure 2:
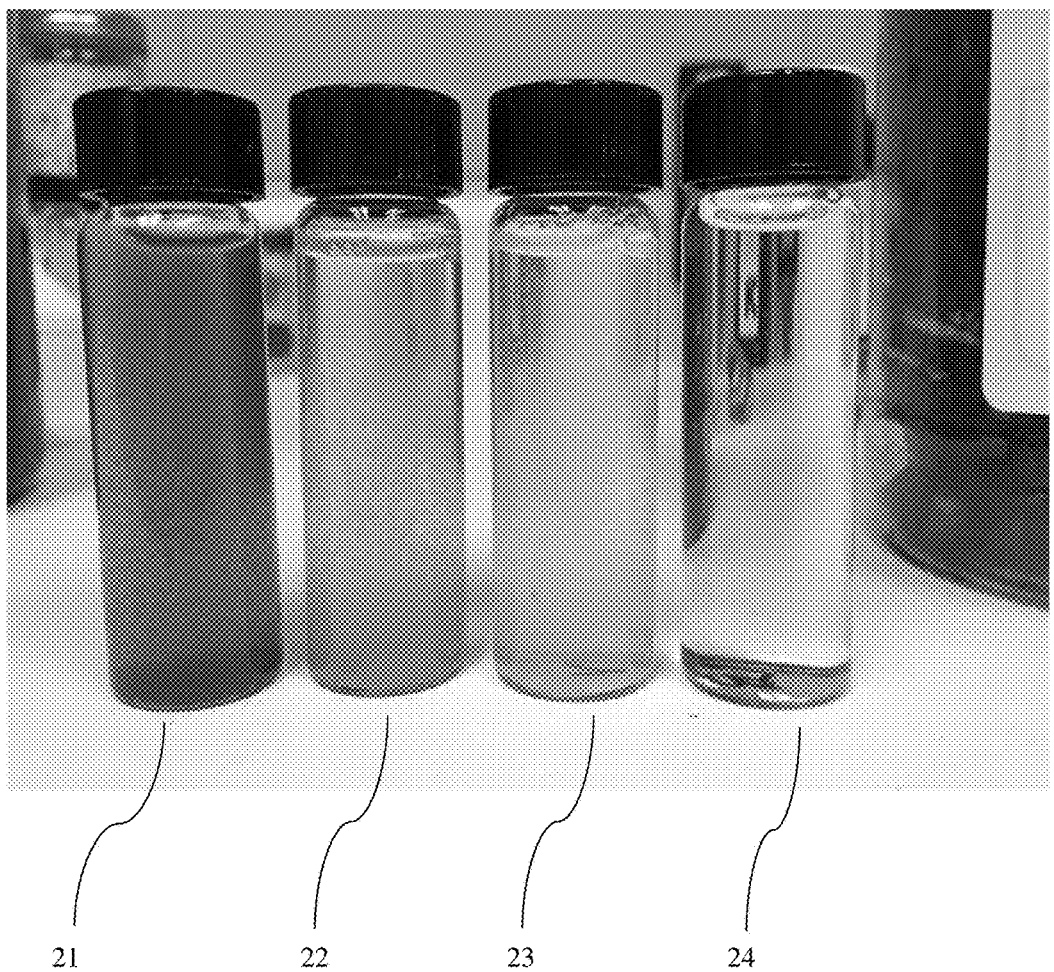
FIG. 2 is a photo showing samples during treatment of waste water from a bean processing operation.

In reference to FIG. 2, 1,000 mL of bean processing waste water containing solid matter ("bean waste") is collected. An aliquot of the untreated bean waste (21) is depicted in FIG. 2. As can be seen in FIG. 2, the untreated bean waste (21) contains dark solid matter.

In a 1,000 mL beaker, 0.2 grams of chlorine (from calcium hypochlorite and sodium dichloro-s-triazinetrione dehydrate) is added to the bean waste to achieve a concentration 200 ppm chlorine. 40 ppm of Bio-Clean All Natural Flocculant from Bio-Chem Industries, Inc. (Ooltewah, Tenn.) is added to the bean waste. 0.25 ppm No-Phos from Bio-Chem Industries, Inc. (Ooltewah, Tenn.) is also added to the bean waste. The resulting solution is stirred for at least thirty seconds. An aliquot of residual bean waste (22) is depicted in FIG. 2. As can be seen in FIG. 2, the residual bean waste (22) contains less suspended solid matter than the untreated bean waste (21).

Additional chlorine is added to the residual bean waste remaining in the beaker, to achieve a concentration of 400 ppm chlorine. Additional Bio-Clean All Natural Flocculant from Bio-Chem Industries, Inc. (Ooltewah, Tenn.) is also added to the bean waste at a ratio of additional flocculant to additional chlorine of 20%. 0.25 ppm No-Phos from Bio-Chem Industries, Inc. (Ooltewah, Tenn.) is also added to the bean waste. The resulting solution is stirred for at least thirty seconds. An aliquot of residual bean waste (23) is depicted in FIG. 2. As can be seen in FIG. 2, the residual bean waste (23) contains even less suspended solid matter than the previously treated bean waste (22).

Additional chlorine is added to the bean waste in the beaker to achieve a concentration of 800 ppm chlorine. Additional Bio-Clean All Natural Flocculant from Bio-Chem Industries, Inc. (Ooltewah, Tenn.) is also added to the bean waste at a ratio of additional flocculant to additional chlorine of 20%. 0.25 ppm No-Phos from Bio-Chem Industries, Inc. (Ooltewah, Tenn.) is also added to the bean waste. The resulting solution is stirred for at least thirty seconds. An aliquot of the bean waste (24) is depicted in FIG. 2. As can be seen in FIG. 2, the bean waste (24) contains no visible solid waste and may be utilized in irrigation of fields.

Example III

Figure 3:
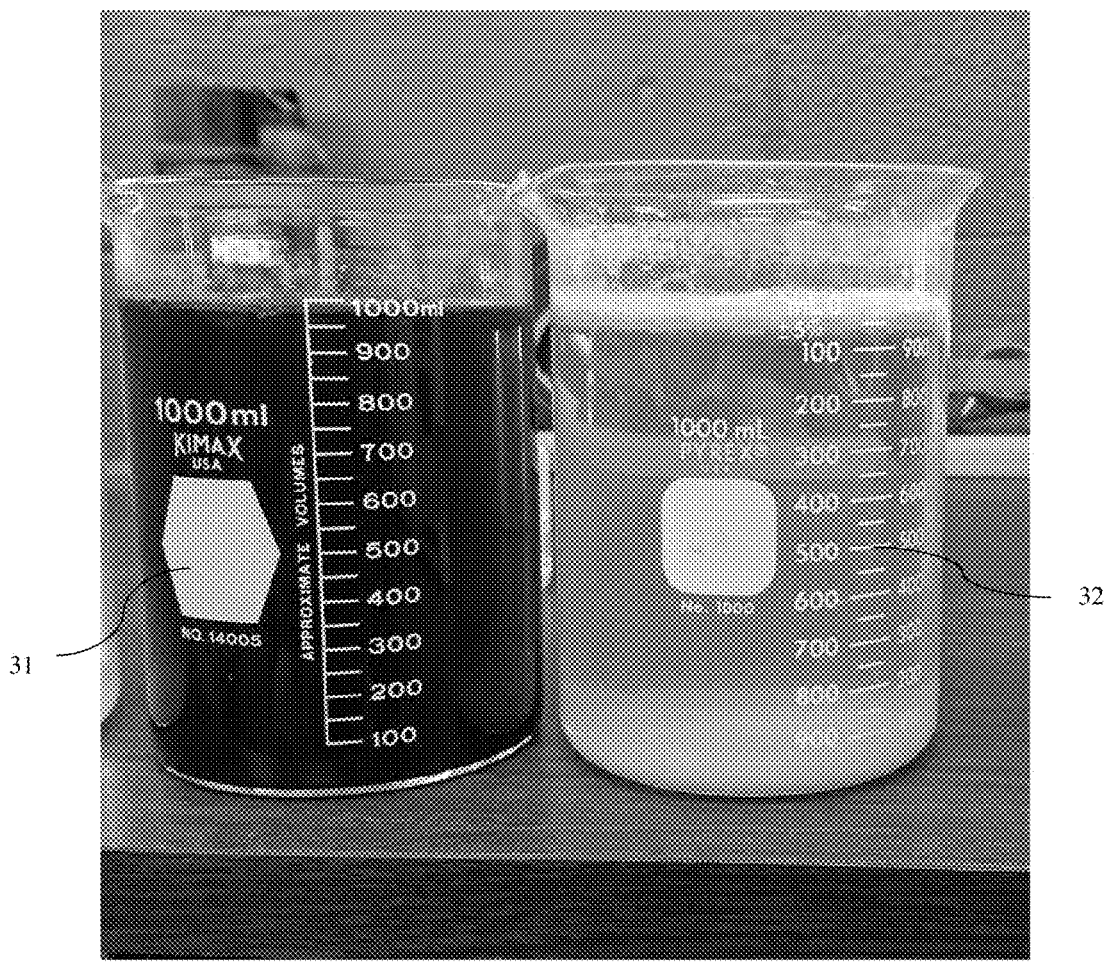
FIG. 3 is a photo showing samples of hog waste before and after treatment.

In reference to FIG. 3, a 1000 ml beaker is filled with 200 ml of hog sludge and 800 ml of hog wastewater with suspended solids. As can be seen in FIG. 3, the untreated hog waste (31) contains dark solid matter. 1,200 ppm chlorine (1.2 grams), 2 ppm Bio-Clean All Natural Flocculant, and 0.25 ppm No-Phos Rare Earth Solution, each from Bio-Chem Industries, Inc. (Ooltewah, Tenn.), is added to the hog wastewater. The resulting mixture is stirred. After about 17 hours of stirring the mixture, all of the solid waste in the hog wastewater appears to be broken down into its constituent components and only foam and murky water remains. An additional 0.125 ppm of Bio-Clean All Natural Flocculant is added to the beaker and the resulting mixture stirred and disperses the foam. An additional 0.125 ppm of Bio-Clean All Natural Flocculant is added to the beaker and the resulting mixture stirred. The water is visibly less murky. Chlorine residuals are measured and it is found that no chlorine residuals remain. Revive NG from Bio-Chem. Industries, Inc. (Ooltewah, Tenn.) is added to the beaker per manufacturer instructions and the resulting mixture is stirred. The solid waste and any suspended solids are completely broken down. As can be seen in FIG. 3, there is no more foam on the top of the solution in the beaker (32). The target clarity is reached and the water may be utilized in irrigation.

Example IV

Treatment of waste discharged from a brewery is undertaken in an activated sludge wastewater treatment plant. The BOD of the brewery waste is tested and found to average 2,400 mg/L. 800 ppm of chlorine (from a combination of calcium hypochlorite and sodium dichloro-s-triazinetrione dehydrate) and Bio-Clean All Natural Flocculant from Bio-Chem Industries, Inc. (Ooltewah, Tenn.) is at a ratio of flocculant to chlorine of 20% is added at the influent of the wastewater plant where turbulence in an aeration basin bonds flocculant to the solids in the plant. Solids are sent to the clarifier and settled into a sludge blanket and residual solid waste is sent to the Digester. Revive NG (which may optionally be used with Revive S) from Bio-Chem. Industries, Inc. (Ooltewah, Tenn.) and Formula D-500 and Bacteria Supplement D500A for Municipal WWTP, each from USA BlueBook (Waukegan, Ill.) are added to the residual solid waste in the digester according to manufacturer instructions, and the resulting mixture is agitated. The resulting water has a BOD that sufficiently low so that it may be discharged from the treatment plant.

What is claimed is:

1. A solid waste treatment method consisting of the steps of:
   a. chlorinating solid waste having a first biological oxygen demand to produce degraded and sterilized solid waste and residual solid waste;
   b. measuring the residual solid waste for chlorine residuals, and if residual chlorine is:
      i) present, dechlorinating the residual solid waste to produce dechlorinated residual solid waste; or
      ii) not present, determining that the residual solid waste is dechlorinated residual solid waste;
   c. adding a flocculating composition to the dechlorinated residual solid waste to solubilize the dechlorinated residual solid waste;
   d. inoculating the dechlorinated residual solid waste with bacteria, selected from the group of aerobic bacteria, facultative bacteria and combinations thereof, wherein the bacteria biodegrade the dechlorinated residual solid waste.

2. The solid waste treatment method of claim 1, wherein the flocculating composition neutralizes the pH of the dechlorinated residual solid waste.

3. The solid waste treatment method of claim 1, wherein chlorination comprises adding chlorine to the solid waste at a concentration of at least from about 100 parts per million to about 3,000 parts per million.

4. The solid waste treatment method of claim 1, wherein the bacteria biodegrade the dechlorinated residual solid waste to reaction products of water and gas.

5. The solid waste treatment method of claim 4, wherein the water is characterized by a second biochemical oxygen demand that is at least about 50% less than the first biochemical oxygen demand.

6. The solid waste treatment method of claim 1, wherein the step of chlorinating the solid waste kills at least about 95% of microbes contained in the solid waste.

7. The solid waste treatment method of claim 1, wherein the bacteria are selected from the group of aerobic bacteria, facultative bacteria and combinations thereof.

8. The solid waste treatment method of claim 1, wherein the solid waste is generated from a beer brewing process.

9. A solid waste treatment method consisting of the steps of:
   a. at least partially degrading and at least partially sterilizing the solid waste by adding chlorine to the solid waste to create residual solid waste;
   b. neutralizing the residual solid waste by adding a flocculating composition to the residual solid waste;
   c. inoculating the neutralized residual solid waste with bacteria selected from the group of aerobic bacteria, facultative bacteria and combinations thereof;
   d. biodegrading the neutralized residual waste with the bacteria;
   e. agitation of the waste in steps a through d; and
   f. dechlorinating the residual solid waste.

10. The solid waste treatment method of claim 9, wherein the bacteria biodegrade the residual solid waste to create water and gas.

11. The solid waste treatment method of claim 10, wherein the water is characterized by a second biochemical oxygen demand that is at least about 50% less than the first biochemical oxygen demand.

12. The solid waste treatment method of claim 10, wherein the water is characterized by a second biochemical oxygen demand that is at least about 80% less than the first biochemical oxygen demand.

13. The solid waste treatment method of claim 9, wherein chlorine is added to the solid waste at a concentration of at least from about 100 parts per million to about 3,000 parts per million.

14. The solid waste treatment method of claim 9, wherein the chlorine is added to the solid waste at a concentration of at least about 300 parts per million to about 2,000 parts per million.

15. A method of solid waste treatment, wherein the solid waste as has a first BOD, the method consisting essentially of the steps of:
   a. partially degrading and at least partially sterilizing the solid waste by adding chlorine to the solid waste to create residual solid waste;
   b. adding a flocculating composition to the residual solid waste;
   c. neutralizing the pH of the residual solid waste;
   d. inoculating the residual solid waste with bacteria selected from the group of aerobic bacteria, facultative bacteria and combinations thereof; and
   e. biodegrading the neutralized residual waste with the bacteria to produce water having a second BOD that is at least 50% less than the first BOD.

* * * * *